United States Patent [19]

Kurahashi et al.

[11] Patent Number: 6,153,763
[45] Date of Patent: Nov. 28, 2000

[54] 1,2,3-BENZOTHIADIAZOLE DERIVATIVES

[75] Inventors: Yoshio Kurahashi, Oyama; Haruko Sawada, Yuki; Taro Kinbara, Oyama; Yasuo Araki, Kaminokawa-machi; Koichi Moriya, Minamikawachi-machi; Koichi Ishikawa; Asami Motonaga, both of Oyama, all of Japan

[73] Assignee: Nihon Bayer Agrochem K.K.

[21] Appl. No.: 09/175,278

[22] Filed: Oct. 20, 1998

Related U.S. Application Data

[62] Division of application No. 08/886,305, Jul. 1, 1997, Pat. No. 5,869,508.

[30]     Foreign Application Priority Data

Jul. 5, 1996    [JP]    Japan ...................................... 8-194074

[51] Int. Cl.[7] ..................... C07D 233/61; C07D 233/60; C07D 233/58
[52] U.S. Cl. .......................................................... 548/333.5
[58] Field of Search .......................................... 548/333.5

[56]              References Cited

U.S. PATENT DOCUMENTS

| | | |
|---|---|---|
| 4,931,581 | 6/1990 | Schurter et al. . |
| 5,051,436 | 9/1991 | Kunz et al. . |
| 5,190,928 | 3/1993 | Schurter et al. . |
| 5,229,384 | 7/1993 | Kunz et al. . |
| 5,248,683 | 9/1993 | Brunner et al. . |
| 5,260,423 | 11/1993 | Kunz et al. . |
| 5,304,652 | 4/1994 | Kunz et al. . |
| 5,384,321 | 1/1995 | Kunz et al. . |
| 5,523,311 | 6/1996 | Schurter et al. . |
| 5,616,590 | 4/1997 | Maetzke . |

FOREIGN PATENT DOCUMENTS

| | | |
|---|---|---|
| 313512 | 4/1989 | European Pat. Off. . |
| 502473 | 9/1992 | European Pat. Off. . |
| 517660 | 12/1992 | European Pat. Off. . |
| 96/11906 | 4/1996 | WIPO . |

OTHER PUBLICATIONS

J. Chem. Soc., 1971, E. Haddock and P. Kirby, "1,2,3–Benzothiadiazoles. Part V.[1] The Rearrangement of Diazonium Salts derived from 7–Aminobenzisothiazoles", pp. 3994–3999.

J. Chem. Soc. (C), 1970, P. Kirby, et al. "1,2,3–Benzothiadiazoles. Part 1. A Simplified Synthesis of 1,2,3–Benzothiadiazoles", pp. 2250–2253.

J. Chem. Soc., 1967, J.H. Davies and P. Kirby, "A Novel Synthesis of Hydroxy–1,2,3–benzothiadiazoles", pp. 321–323.

J. Chem. Soc., 1970, E. Haddock and P. Kirby, "1,2,3–Benzothiadiazoles. Part II.[1] A Novel Rearrangement of Diazonium Salts derived from 7–Amino–1,2,3–Benzothiadiazoles", pp. 2514–2518.

*Primary Examiner*—Patricia L. Morris
*Attorney, Agent, or Firm*—Norris, McLaughlin & Marcus, P.A.

[57]              ABSTRACT

Novel 1,2,3-benzothiadiazole derivatives of the formula

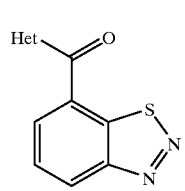

(I)

in which

Het has the meanings set forth in the specification, and addition products thereof with an acid or metal salt are very effective for the control of undesired microorganisms.

Novel intermediates of the formulae

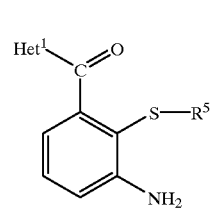

(IV)

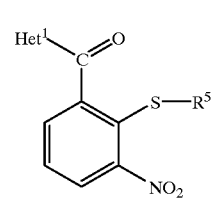

(VI)

and

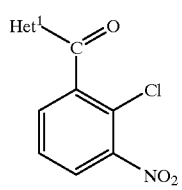

(VII)

in which

Het[1] and R[5] have the meanings given in the specification.

3 Claims, No Drawings

1,2,3-BENZOTHIADIAZOLE DERIVATIVES

This is a division of application Ser. No. 08/886,305, filed Jul. 1, 1997, now U.S. Pat. No. 5,869,508, issued Feb. 9, 1999.

The present invention relates to novel 1,2,3-benzothiadiazole derivatives, to processes for their preparation, and to their use as microbicides. Further, the invention relates to novel intermediates and to processes for their preparation.

It has already been known that certain 1,2,3-benzothiadiazole derivatives have fungicidal properties (see Japanese published patent applications Hei 1-90 176, Hei 3-169 872, Hei 5-97 829, Hei 5-194 450, Hei 8-53 464 and GB-A 1 176 799). The activity of these substances, however, is not always satisfactory when they are applied at low dosages.

Further, some methods for synthesizing 1,2,3-benzothiadiazole derivatives have already been described (see J. Chem. Soc. 1967, 321–323, J. Chem. Soc. 1970, 2514–2518, J. Chem. Soc. 1970, 2250–2252 and J. Chem. Soc. 1971, 3994–3999). However, the availability of additional processes for the preparation of such compounds is desired.

There have been found novel 1,2,3-benzothiadiazole derivatives of the formula

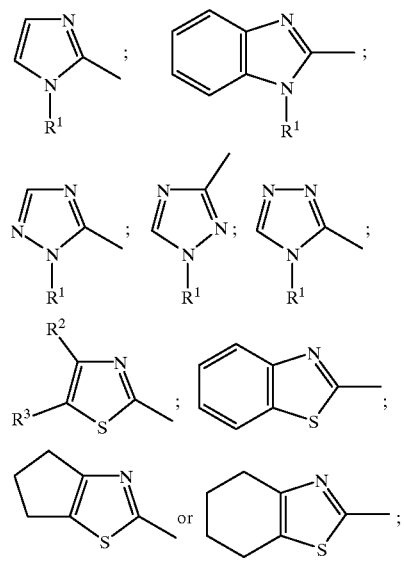

(I)

in which
Het is wherein
R$^1$ is hydrogen, optionally substituted C$_{1-6}$ alkyl, optionally substituted C$_{2-6}$ alkenyl or optionally substituted phenyl and
R$^2$ and R$^3$ independently of each other are hydrogen or optionally substituted C$_{1-6}$ alkyl, and acid addition salts and metal salts complexes thereof It has furthermore been found that 1,2,3-benzothiadiazole derivatives of the formula (I) and acid addition salts and metal salt complexes thereof can be prepared by a) reacting 1,2,3-benzothiadiazolylcarbonyl halides of the formula

(II)

in which
Hal is chlorine or bromine,
with heterocycles of the formula

Het$^1$—H (III)

in which
Het$^1$ represents

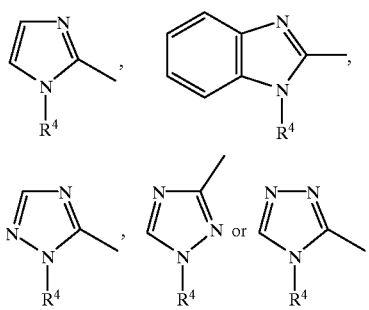

wherein
R$^4$ is optionally substituted C$_{1-4}$ alkyl, optionally substituted C$_{2-6}$ alkenyl or optionally substituted phenyl,
or
Het$^1$ represents

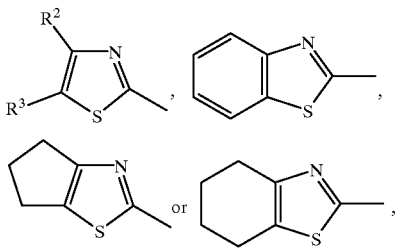

wherein
R$^2$ and R$^3$ have the above-mentioned meanings,
in the presence of an inert diluent and, if appropriate, in the presence of an acid binder,
or b) reacting phenyl derivatives of the formula $$\text{Het}^1-\overset{O}{\underset{\|}{C}}-\underset{NH_2}{\overset{S-R^5}{\bigcirc}} \quad (IV)$$

in which
Het¹ has the above-mentioned meanings and
$R^5$ is hydrogen, $C_{1-4}$ alkyl, benzyl or acetyl,
with nitrous acid or a salt thereof,
in the presence of an inert diluent under acidic conditions, or c) reacting 1,2,3-benzothiadiazole derivatives of the formula $$\text{Het}^2-\overset{O}{\underset{\|}{C}}-\text{(benzothiadiazole)} \quad (Ia)$$

in which
Het² is (imidazole-N-CH₂—OCH₃), (benzimidazole-N-CH₂—OCH₃), (triazole-N-CH₂—OCH₃), (triazole-N-CH₂—OCH₃) or (triazole-N-CH₂—OCH₃), with an acid and, if appropriate,
in the presence of an inert diluent, or d) reacting 1,2,3-benzothiadiazole derivatives of the formula $$\text{Het}^3-\overset{O}{\underset{\|}{C}}-\text{(benzothiadiazole)} \quad (Ib)$$

in which

Het³ is (imidazole-NH), (benzimidazole-NH), (triazole-NH), (triazole-NH) or (triazole-NH), with halogeno compounds of the formula $$R^6-Hal^1 \quad (V)$$

in which
$R^6$ is optionally substituted $C_{1-6}$ alkyl or optionally substituted $C_{2-6}$ alkenyl and
$Hal^1$ is chlorine, bromine or iodine,
in the presence of an inert diluent and, if appropriate,
in the presence of an acid binder, and, if appropriate, adding an acid or a metal salt onto the 1,2,3-benzothiadiazole derivatives of the formula (I) thus obtained.

Finally, it has been found that the 1,2,3-benzothiadiazole derivatives of the formula (I) and acid addition salts and metal salt complexes thereof are outstandingly active as microbicides, which can be used in agriculture and horticulture. They can either be used for directly combating undesired microorganisms, such as phytopathogenic fungi and bacteria or for inducing in the plant bodies themselves resistance to phytopathogenic fungi and bacteriae.

Surprisingly, the compounds according to the invention have a much better fungicidal activity than the already known compounds which are structurally most similar and have the same type of action.

In the present context, "alkyl" represents straight-chain or branched groups. The term "alkyl" includes, for example, methyl, ethyl, propyl, isopropyl and n- (iso-, sec-, tert-) butyl. Said "alkyl" may be substituted and the substituents thereof include halogen, such as fluoro, chloro or bromo, cyano, alkoxy, such as methoxy, ethoxy or propoxy, alkylthio, such as methylthio or ethylthio, alkoxycarbonyl, such as methoxycarbonyl or ethoxycarbonyl, and phenyl.

The term "alkenyl", in the present context, also represents straight-chain or branched groups. It includes, for example, vinyl, allyl, isopropenyl and 1-methyl-2-propenyl.

Formula (I) provides a general definition of the 1,2,3-benzothiadiazole derivatives according to the invention. Preferred compounds of the formula (I) are those, in which Het is (imidazole-N-R¹); (benzimidazole-N-R¹);

(triazole-N-R¹); (triazole-N-R¹); (triazole-N-R¹);

-continued

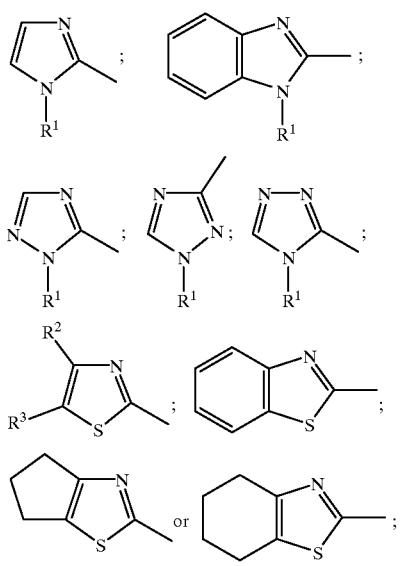

wherein
R¹ is hydrogen, $C_{1-4}$ alkyl, $C_{1-4}$ haloalkyl, phenyl-$C_{1-4}$ alkyl, cyano-$C_{1-4}$ alkyl, $C_{1-2}$-alkoxy-$C_{1-4}$ alkyl, $C_{1-2}$-alkylthio-$C_{1-4}$ alkyl, $C_{1-2}$-alkoxycarbonyl-$C_{1-4}$ alkyl, $C_{2-4}$ alkenyl, phenyl, halogen substituted phenyl or $C_{1-4}$ alkyl substituted phenyl and
R² and R³ independently of each other are hydrogen or $C_{1-4}$ alkyl.

Particularly preferred 1,2,3-benzothiadiazole derivatives of the formula (I) are those, in which
Het is wherein
R¹ is hydrogen, methyl, ethyl, propyl, isopropyl, butyl, cyanomethyl, 2-cyanoethyl, 1-cyano-ethyl, 3-cyano-propyl, methoxymethyl, ethoxymethyl, methylthiomethyl, methoxycarbonyl-ethyl, ethoxycarbonyl-methyl, ethoxycarbonyl-ethyl, fluoromethyl, difluoromethyl, trifluoromethyl, chloromethyl, benzyl, phenyl, chlorophenyl, methylphenyl, vinyl, allyl or but-3-en-1-yl, and
R² and R³ independently of each other are hydrogen, methyl, ethyl, propyl or isopropyl.

Addition products of acids and those 1,2,3-benzothiadiazole derivatives of the formula (I), in which Het has the meanings, which have already been mentioned as preferred for this radical, are also preferred compounds according to the invention.

The acids which can be added on include, preferably, hydrogen halide acids, such as, for example, hydrochloric acid and hydrobromic acid, in particular hydrochloric acid, and, furthermore, phosphoric acid, nitric acid, sulphuric acid, mono- and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example p-toluenesulphonic acid, 1,5-naphthalenedisulphonic acid or camphorsulphonic acid, as well as saccharin and thiosaccharin.

Addition products of salts of metals of main groups II to IV and of sub-groups I and II and IV to VIII of the periodic table of the elements and those 1,2,3-benzothiadiazole derivatives of the formula (I), in which Het has the meanings, which have already been mentioned as preferred for this radical, are also preferred compounds according to the invention.

Salts of copper, zinc, manganese, magnesium, tin, iron and nickel are particularly preferred here. Possible anions of these salts are those which are derived from those acids which lead to physiologically acceptable addition products. Particularly preferred acids of this type are, in this connection, the hydrogen halide acids, such as, for example, hydrochloric acid and hydrobromic acid, and, furthermore, phosphoric acid, nitric acid and sulphuric acid.

Specific examples of 1,2,3-benzothiadiazole derivatives of the formula (I) are listed in the following Table 1.

TABLE 1

(I)

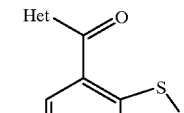

| Het | R¹, R² or R³ |
|---|---|
| 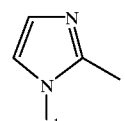 | H<br>$CH_2CH_2CO_2CH_3$<br>$CH_3$<br>$CH_2CO_2CH_2CH_3$<br>$CH_2CH_3$<br>$CH=CH_2$<br><br>$CH_2CH_2CH_3$<br>$CH_2CH=CH_2$<br>$CH(CH_3)_2$<br>$CH_2CH_2CH=CH_2$<br>$CH_2CH_2CH_2CH_3$<br>$CH_2C_6H_5$<br>$CH_2OCH_3$<br>$C_6H_5$<br>4-Cl—$C_6H_4$<br>2-$CH_3$—$C_6H_4$<br>$CH_2SCH_3$<br>$CHF_2$<br>$CH_2CN$<br>$CF_3$<br>$CH_2CH_2CN$ |
| 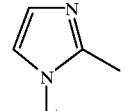 | $CH_2Cl$<br>$CH_2CH_2CH_2CN$<br>$CH_2F$<br>$CH(CH_3)CN$<br>$CH_2CO_2CH_3$ |
| 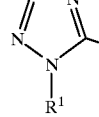 | H<br>$CH_2CH_2CO_2CH_3$<br>$CH_2CH_2CO_2CH_2CH_3$<br>$CH_2CH_3CH=CH_2$<br>$CH_2CH_2CH_3$<br>$CH_2CH=CH_2$ |

TABLE 1-continued

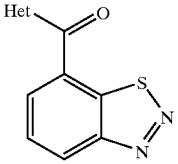
(I)

| Het | R¹, R² or R³ |
|---|---|
| 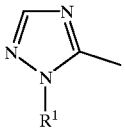 | CH(CH$_3$)$_2$<br>CH$_2$CH$_2$CH=CH$_2$<br>CH$_2$CH$_2$CH$_2$CH$_3$<br>CH$_2$C$_6$H$_5$<br>CH$_2$OCH$_3$<br>C$_6$H$_5$<br>4-Cl—C$_6$H$_4$<br>CH$_2$SCH$_3$<br>CHF$_2$<br>CH$_2$CN<br>CF$_3$<br>CH$_2$CH$_2$CN<br><br>CH$_2$Cl<br>CH$_2$CH$_2$CH$_2$CN<br>CH$_2$F<br>CH(CH$_3$)CN<br>CH$_2$CO$_2$CH$_3$ |
| 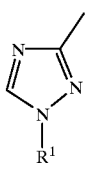 | H<br>CH$_2$CH$_2$CO$_2$CH$_3$<br>CH$_3$<br>CH$_2$CO$_2$CH$_2$CH$_3$<br>CH$_2$CH$_3$<br>CH$_2$CH$_2$CH$_3$<br>CH$_2$CH=CH$_2$<br><br>CH(CH$_3$)$_2$<br>CH$_2$CH$_2$CH=CH$_2$<br>CH$_2$CH$_2$CH$_2$CH$_3$<br>CH$_2$C$_6$H$_5$<br>CH$_2$OCH$_3$<br>C$_6$H$_5$<br>CH$_2$SCH$_3$<br>CHF$_2$<br>CH$_2$CN<br>CF$_3$<br>CH$_2$CH$_2$CN<br>CH$_2$Cl<br><br>CH$_2$CH$_2$CH$_2$CN<br>CH$_2$F<br>CH(CH$_3$)CN<br>CH$_2$CO$_2$CH$_3$ |
| 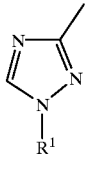 | CH$_3$<br>CH$_2$CH$_3$<br>CH(CH$_3$)$_2$<br>C$_6$H$_5$ |
| 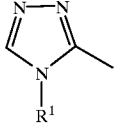 | R² = H, R³ = H<br>R² = CH$_3$, R³ = H<br>R² = H, R³ = CH$_3$<br>R² = CH$_3$, R³ = CH$_3$<br>R² = CH$_2$CH$_3$, R³ = H<br>R² = CH$_2$CH$_2$CH$_3$, R³ = H<br>R² = CH(CH$_3$)$_2$, R³ = H<br>R² = C(CH$_3$)$_2$, R³ = CH$_3$<br>R² = CH$_2$CH$_3$, R³ = CH$_3$ |
| | R² = C(CH$_3$)$_3$, R³ = CH$_3$ |
| 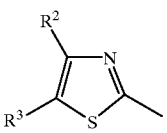 | H<br>CH$_3$ |
| 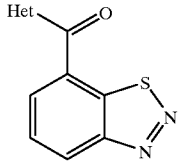 | CH$_2$OCH$_3$<br>CH$_2$CN |
| 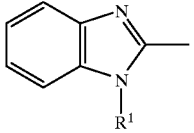 | — |
| 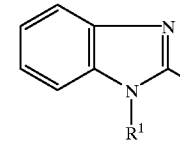 | — |
| 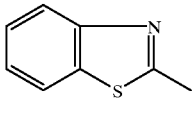 | — |

If 7-chlorocarbonyl-1,2,3-benzothiadiazole and 1-methyl-imidazole are used as starting materials, the course of process (a) according to the invention can be illustrated by the following formula scheme

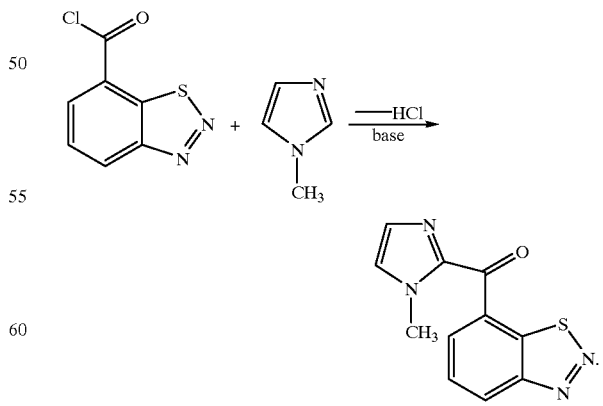

If 2-(3'-amino-2'-benzylthio-benzoyl)-1-methyl-imidazole and nitrous acid are used as starting materials, the course of process (b) according to the invention can be illustrated by the following formula scheme

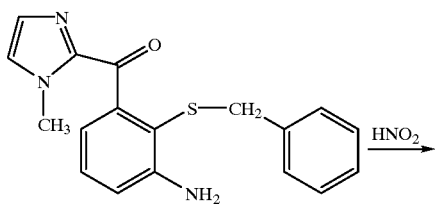

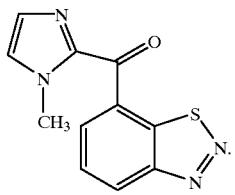

If 5-(1',2',3'-benzothiadiazol-7'-yl)-carbonyl-1-methoxymethyl-1,2,4-triazole and concentrated hydrochloric acid are used as starting materials, the course of process (c) according to the invention can be illustrated by the following formula scheme

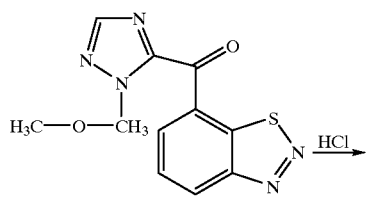

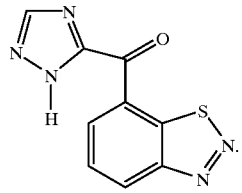

If 3-(1',2',3'-benzothiadiazol-7'-yl)-carbonyl-1,2,4-triazole and methyl iodide are used as starting materials, the course of process (d) according to the invention can be illustrated by the following formula scheme

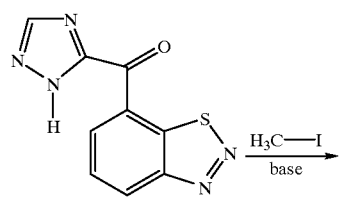

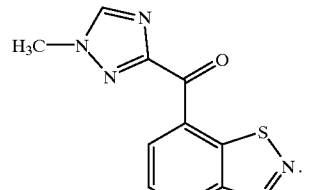

Formula (II) provides a general definition of the 1,2,3-benzothiadiazolyl-carbonyl halides required as starting materials for carrying out process (a) according to the invention. In this formula, Hal denotes chlorine or bromine.

Specific examples of the compounds of the formula (II) are 7-chlorocarbonyl-1,2,3-benzothiadiazole and 7-bromocarbonyl-1,2,3-benzothiadiazole.

The 1,2,3-benzothiadiazolyl-carbonyl halides of the formula (II) are known (see Japanese published patent application Het 1-90 176).

Formula (III) provides a general definition of the heterocycles required as reaction components in carrying out process (a) according to the invention.

In this formula, $Het^1$ preferably is

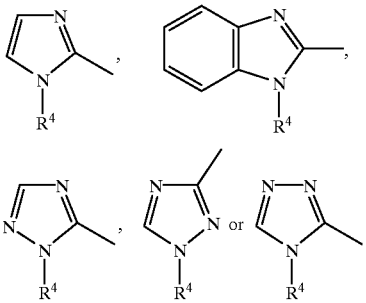

wherein $R^4$ preferably is $C_{1-4}$ alkyl, $C_{1-4}$-haloalkyl, phenyl-$C_{1-4}$ alkyl, cyano-$C_{1-4}$ alkyl, $C_{1-2}$-alkoxy-$C_{1-4}$ alkyl, $C_{1-2}$ alkylthio-$C_{1-4}$ alkyl, $C_{1-2}$-alkoxycarbonyl-$C_{1-4}$ alkyl, $C_{2-4}$ alkenyl, phenyl, halogen substituted phenyl or $C_{1-4}$ alkyl substituted phenyl, or $Het^1$ is

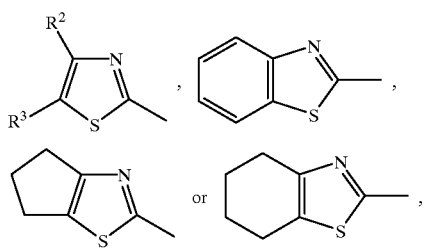

wherein $R^2$ and $R^3$ independently of each other are hydrogen or $C_{1-4}$ alkyl.

$Het^1$ particularly preferably is

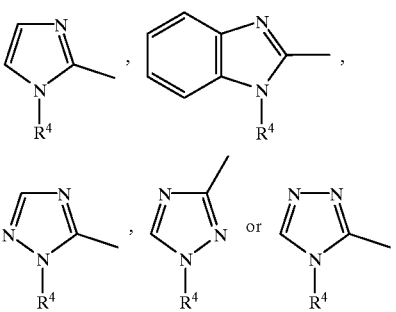

wherein $R^4$ particularly preferably is methyl, ethyl, propyl, isopropyl, butyl, cyanomethyl, 2-cyano-ethyl, 1-cyano-ethyl, 3-cyano-propyl, methoxymethyl, ethoxymethyl, methylthiomethyl, methoxycarbonyl-ethyl, ethoxy-carbonyl-methyl, ethoxycarbonyl-ethyl, fluoromethyl, difluoromethyl, trifluoromethyl, chloromethyl, benzyl, phenyl, chlorophenyl, methyl-phenyl, vinyl, allyl or but-3-en-1-yl, $Het^1$ is

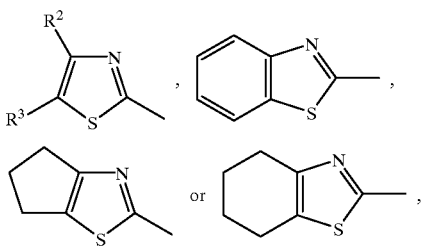

wherein $R^2$ and $R^3$ independently of each other are hydrogen, methyl, ethyl, propyl, isopropyl or tert-butyl.

The following compounds may be mentioned as examples of heterocycles of the formula (III):

1-methylimidazole, 1-ethylimidazole, 1-n-propylimidazole, 1-isopropylimidazole, 1-vinylimidazole, 1-cyanomethylimidazole, 1-(2-cyanoethyl)-imidazole, 1-difluoromethylimidazole, 1-(methoxymethyl)-imidazole, 1-(methoxycarbonylmethyl)-imidazole, 1-phenylimidazole, thiazole, 4-methylthiazole, 5-methylthiazole, 4,5-dimethylthiazole, benzothiazole, 4,5,6,7-tetrahydrobenzothiazole, 1-methyl-1,2,4-triazole, 1-ethyl-1,2,4-triazole, 1-n-propyl-1,2,4-triazole, 1-isopropyl-1,2,4-triazole, 4-methyl1,2,4-triazole, 1-difluoromethyl-1,2,4-triazole, 1-cyanomethyl-1,2,4-triazole, 1-(2-cyanoethyl)-1,2,4-triazole, 1-methoxymethyl-1,2,4-triazole, 1-methylthiomethyl-1,2,4-triazole, 1-vinyl-1,2,4-triazole, 1-phenyl-1,2,4-triazole and 1-benzyl-1,2,4-triazole.

The heterocycles of the formula (III) are known.

Formula (IV) provides a general definition of the phenyl derivatives, which are required as starting materials for carrying out process (b) according to the invention. In this formula, $Het^1$ preferably has those meanings, which have already been mentioned as preferred for this substituent. $R^5$ preferably is hydrogen, methyl, isopropyl, benzyl or acetyl. $R^5$ is particularly preferably benzyl.

The phenyl derivatives of the formula (IV) are novel. They can be prepared by e) reacting nitro-phenyl derivatives of the formula

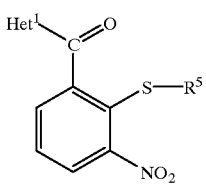

(VI)

in which $Het^1$ and $R^5$ have the above-mentioned meanings, with reducing agents, in the presence of an inert diluent and, if appropriate, in the presence of a catalyst.

The nitro-phenyl derivatives of the formula (VI) are novel too. They can be prepared by f) reacting chloro-nitro-phenyl derivatives of the formula

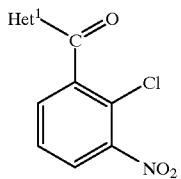

(VII)

in which $Het^1$ has the above mentioned meanings, with sulphur compounds of the formula $$HS-R^5 \quad (VIII)$$

in which $R^5$ has the above mentioned meanings, in the presence of an inert diluent and, if appropriate, in the presence of an acid binder.

The chloro-nitro-phenyl derivatives of the formula (VII) are also novel. They can be prepared by g) reacting 2-chloro-3-nitro-benzoyl chloride of the formula

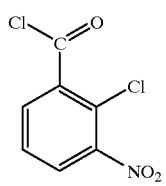

(IX)

with a heterocycle of the formula $$Het^1-H \quad (III)$$

in which $Het^1$ has the above mentioned meanings, in the presence of an inert diluent and, if appropriate, in the presence of an acid binder.

The 2-chloro-3-nitro-benzoyl chloride of the formula (IX) is a known compound.

The heterocycles of the formula (III) are also known. Specific examples include imidazole, benzimidazole, 1,2,4-triazole, thiazole, 4-methyl-thiazole, 5-methyl-thiazole, 4,5-dimethylthiazole, benzothiazole, 4,5,6,7-tetrahydrobenzothiazole as well as the compounds specifically mentioned as examples of heterocycles of the formula (III) above.

Process (g) is carried out under reaction conditions corresponding to that of process (a) (see below).

Processes (e) and (f) are carried out under reaction conditions corresponding to those, which are known from the Japanese published patent application Hei 1-90 176.

Formula (VIII) provides a general definition of the sulphur compounds, which are required as reaction components for carrying out process (f). In this formula, $R^5$ preferably has those meanings, which have already been mentioned as preferred for this substituent.

Specific examples of sulphur compounds of the formula (VIII) include benzylmercaptan, methylmercaptan and isopropylmercaptan.

The sulphur compounds of the formula (VIII) are known.

Formula (Ia) provides a general definition of the 1,2,3-benzothiadiazole derivatives, which are required as starting materials for carrying out process (c) according to the invention. In this formula, $Het^2$ preferably has the meanings, which have already been mentioned above for this radical.

Specific examples of the compounds of the formula (Ia) include 2-(1',2',3'-benzothiadiazol-7'-yl)-carbonyl-1-methoxymethylimidazole, 2-(1',2',3'-benzothiadiazol-7'-yl)-carbonyl-2-methoxymethylbenzimidazole and 5-(1',2',3'-benzothiadiazol-7'-yl)-carbonyl-1-methoxymethyl-1,2,4-triazole.

The 1,2,3-benzothiadiazole derivatives of the formula (Ia) are compounds according to the invention, which can be prepared according to process (a) mentioned above.

Formula (Ib) provides a general definition of the 1,2,3-benzothiadiazole derivatives, which are required as starting materials for carrying out process (d) according to the invention. In this formula, $Het^3$ preferably has the meanings, which have already been mentioned above for this radical.

Specific examples of the compounds of the formula (Ib) include 2-(1',2',3'-benzothiadiazol-7'-yl)-carbonylimidazole, 2-(1',2',3'-benzothiadiazol-7'-yl)-carbonylbenzimidazole and 5-(1',2',3'-benzothiadiazol-7'-yl)-carbonyl-1,2,4-triazole.

The 1,2,3-benzothiadiazole derivatives of the formula (Ib) are compounds according to the invention, which can be prepared according to processes (b) and (c) mentioned above.

Formula (V) provides a general definition of the halogeno compounds, which are required as reaction components for carrying out process (d) according to the invention. In this formula, $R^6$ preferably is $C_{1-4}$ alkyl, $C_{1-4}$ haloalkyl, phenyl $C_{1-4}$ alkyl, cyano-$C_{1-4}$ alkyl, $C_{1-2}$ alkoxy-$C_{1-4}$ alkyl, $C_{1-2}$ alkylthio-$C_{1-4}$ alkyl, $C_{1-2}$-alkoxycarbonyl-$C_{1-4}$ alkyl or $C_{2-4}$ alkenyl and $Hal^1$ preferably is chlorine, bromine or iodine.

$R^6$ particularly preferably is methyl, ethyl, propyl, isopropyl, butyl, cyano-methyl, 2-cyano-ethyl, 1-cyano-ethyl, 3-cyano-propyl, methoxymethyl, ethoxymethyl, methylthiomethyl, methoxycarbonyl-ethyl, ethoxycarbonyl-methyl, ethoxycarbonyl-ethyl, fluoromethyl, difluoromethyl, trifluoromethyl, chloromethyl, vinyl, allyl or but-3-en-1-yl, and $Hal^1$ particularly preferably is chlorine, bromine or iodine.

Specific examples of halogeno compounds of the formula (V) include methyl iodide, ethyl iodide, propyl iodide, isopropyl iodide, cyanomethyl iodide, methoxymethyl chloride, methylthiomethyl chloride, chlorodifluoromethane, cyanoethyl bromide, allyl bromide, methyl chloroacetate, ethyl chloroacetate, ethyl-3-chloropropionate, ethyl 2-chloropropionate, methyl 3-chloropropionate and methyl 2-chloropropionate.

The halogeno compounds of the formula (V) are known.

All inert organic solvents customary for such reactions can be used as diluents in carrying out process (a) according to the invention. Suitable solvents preferably are aliphatic, alicyclic or aromatic hydrocarbons (which may be optionally chlorinated), such as pentane, hexane, cyclohexane, petroleum ether, ligroin, benzene, toluene, xylene, dichloromethane, chloroform, carbon tetrachloride, 1,2-dichloroethane, chlorobenzene or dichlorobenzene; ethers such as diethyl ether, methyl ethyl ether, diisopropyl ether, dibutyl ether, dioxane, dimethoxyethane (DME), tetrahydrofuran (THF) or diethylene glycol dimethyl ether (DGM); nitriles such as acetonitrile, propionitrile or acrylonitrile; esters such as ethyl acetate or amyl acetate; acid amides such as dimethylformamide (DMF), dimethylacetamide (DMA), N-methylpyrrolidone, 1,3-dimethyl-2-imidazolidinone or hexamethylphosphoric triamide (HMPA); and sulfones and sulfoxides such as dimethyl sulfoxide (DMSO) or sulfolan; and bases such as pyridine.

The process (a) can be carried out in the presence of an acid binding agent. Suitable acid binding agents are organic bases, for example, tertiary amines, dialkylaminoanilines and pyridines, such as triethylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo[2,2,2]octane (DABCO) or 1,8-diazabicyclo[5,4,0]undec-6-ene (DBU).

In carrying out process (a) according to the invention, the reaction temperatures can be varied within a substantially wide range. The reaction is generally carried out at a temperature between about −75° C. and about +150° C. preferably between about 0° C. and about 100° C.

Process (a) according to the invention is generally carried out under atmospheric pressure but, if desired, can also be carried out under elevated or reduced pressure.

In carrying out process (a) according to the invention, in general 1 mol of a 1,2,3-benzothiadiazolyl-carbonyl halide of the formula (II) is reacted with 0.1 to 10 mol of a heterocycle of the formula (III) in the presence of a diluent, such as dichloromethane, and, if appropriate, in the presence of an acid binder, such as pyridine. Working up is carried out by customary methods.

Process (b) according to the invention can also be carried out in the presence of all diluents customary for such reactions. Suitable diluents preferably are water, hydrochloric acid, acetic acid and sulfuric acid; aliphatic, alicyclic or aromatic hydrocarbons (which may be optionally chlorinated), such as pentane, hexane, cyclohexane, petroleum ether, ligroin, benzene, toluene, xylene, dichloromethane, chloroform, carbon tetrachloride, 1,2-dichloroethane, chloro-benzene or dichlorobenzene; ethers such as diethyl ether, methyl ethyl ether, diusopropyl ether, dibutyl ether, dioxane, dimethoxyethane (DME), tetrahydrofuran (THT) or diethylene glycol dimethyl ether (DGM); nitriles such as acetonitrile, propionitrile or acrylonitrile; esters such as ethyl acetate or amyl acetate; acid amides such as dimethylformamide (DMF), dimethylacetamide (DMA), N-methylpyrrolidone, 1,3-dimethyl-2-imidazolidinone or hexamethylphosphoric triamide (HNPA); and sulfones and sulfoxides such as dimethyl sulfoxide (DMSO) or sulfolan.

In carrying out process (b) according to the invention, the reaction temperatures can be varied within a substantially wide range. The reaction is generally carried out at a temperature between about −20° C. and about +100° C., preferably between about 0°πC, and about 80° C.

Process (b) according to the invention is preferably carried out under atmospheric pressure but, if desired, can also be carried out under elevated or reduced pressure.

In carrying out process (b) according to the invention, in general 1 mol of phenyl derivative of the formula (IV) is reacted with 1 to 10 mol of nitrous acid or a salt thereof in the presence of a diluent, such as water, under acidic conditions. Working up is carried out by customary methods.

Process (c) according to the invention can also be carried out in the presence of all diluents customary for such reactions. Suitable diluents preferably are water; aliphatic, alicyclic or aromatic hydrocarbons (which may be optionally chlorinated), such as pentane, hexane, cyclohexane, petroleum ether, ligroin, benzene, toluene, xylene, dichloromethane, chlorfrom, carbon tetrachloride, 1,2-dichloroethane, chlorobenzene or dichlorobenzene; ethers such as diethyl ether, methyl ethyl ether, diisopropyl ether, dibutyl ether, dioxane, dimethoxyethane (DME), tetrahydrofuran (THF) or diethylene glycol dimethyl ether (DGM); ketones such as acetone, methyl ethyl ketone (MEK), methylisopropyl ketone or methyl isobutyl ketone (MIBK); nitriles such as acetonitril, propionitrile or acrylonitrile; alcohols such as methanol, ethanol, isopropanol, butanol or ethylene glycol; esters such as ethyl acetate or amyl acetate; acid amides such as dimethylformamide (DMF), dimethylacetamide (DMA), N-methylpyrrolidone, 1,3-di-methyl-2-imidazolidinone and hexamethylphosphoric triamide (HMPA); and sulfones and sulfoxides such as dimethyl sulfoxide (DMSO) or sulfolan.

Process (c) according to the invention is carried out in the presence of an acidic compound. Suitable acidic compounds preferably are mineral acids such as hydrochloric acid, sulfuric acid, phosphoric acid, hydrobromic acid or sodium hydrogensulfide; organic acids such as formic acid, acetic acid, trifluoroacetic acid, propionic acid, methanesulfonic acid, benzenesulfonic acid or p-toluenesulfonic acid; and organic amine hydrochlorides such as pyridine hydrochloride and triethylamine hydrochloride.

In carrying out process (c) according to the invention, the reaction temperatures can be varied within a substantially wide range. The reaction is generally carried out at a temperature between about −20° C. and about +150° C., preferably between about 0° C. and about 120° C.

Process (c) according to the invention is generally carried out under atmospheric pressure but, if desired, can also be carried out under elevated pressure.

In carrying out process (c) according to the invention, in general 1 mol of a 1,2,3-benzothiadiazole derivative of the formula (Ia) is reacted with an equimolar amount or an excess of an acidic compound, such as concentrated hydrochloric acid, in the presence of a diluent, such as water. Working up is carried out by customary methods.

In carrying out process (d) according to the invention, all inert organic solvents customary for such reactions can be used as diluents. Suitable diluents preferably are aliphatic, alicyclic or aromatic hydrocarbons (which may be optionally chlorinated), such as pentane, hexane, cyclohexane, petroleum ether, ligroin, benzene, toluene, xylene, dichloromethane, chlorfrom, carbon tetrachloride, 1,2-dichloroethane, chlorobenzene or dichlorobenzene; ethers such as diethyl ether, methyl ethyl ether, diisopropyl ether, dibutyl ether, dioxane, dimethoxyethane (DME), tetrahydrofuran (THF) or diethylene glycol dimethyl ether (DGM); ketones such as acetone, methyl ethyl ketone (MEK), methylisopropyl ketone or methyl isobutyl ketone (MIBK); nitriles such as acetonitril, propionitrile or acrylonitrile; alcohols such as methanol, ethanol, isopropanol, butanol or ethylene glycol; esters such as ethyl acetate or amyl acetate; acid amides such as dimethylformamide (DMF), dimethylacetarnide (DMA), N-methylpyrrolidone, 1,3-dimethyl-2-imidazolidinone and hexamethylphosphoric triamide (HMPA); and sulfones and sulfoxides such as dimethyl sulfoxide (DMSO) or sulfolan.

Process (d) according to the invention can also be carried out in the presence of an acid binding agent. Suitable acid binders preferably are inorganic binders, for example, hydroxides, carbonates and bicarbonates of alkali metals or alkaline earth metals, such as sodium hydrogencarbonate, potassium hydrogencarbonate, sodium carbonate, potassium carbonate, lithium hydroxide, sodium hydroxide, potassium hydroxide or calcium hydroxide; alkali metal amides, for example, lithium amide, sodium amide or potassium amide; organic bases, for example, alcoholates, tertiary amines, dialkylaminoanilines and pyridines, such as triethylamine, 1,1,4,4-tetramethylethylenediamine (TMEDA), N,N-dimethylaniline, N,N-diethylaniline, pyridine, 4-dimethylaminopyridine (DMAP), 1,4-diazabicyclo[2,2,2] octane (DABCO) or 1,8-diazabicyclo-[5.4.0]-undec-6-ene (DBU); and organic lithium compounds, for example, methyllithium, n-butyllithium, sec-butyllithium, tert-butyllithium, phenyllithium, dimethylcopperlithium, lithium diisopropylamide, lithium cyclohexylisopropylamide, lithium dicyclohexylamide, n-butyllithium-DABCO, n-butyllithium.DBU and n-butyllithium TMEDA.

In carrying out process (d) according to the invention, the reaction temperatures can be varied within a substantially wide range. The reaction is generally carried out at a temperature between about −70° C. and about +150° C., preferably between about 0° C. and about 120° C.

Process (d) according to the invention is generally carried out under atmospheric pressure but, if desired, can also be carried out under elevated pressure.

In carrying out process (d) according to the invention, in general 1 mol of a 1,2,3-benzothiadiazole derivative of the formula (Ib) is reacted with I to 1.5 mol of a halogeno compound of the formula (V) in the presence of a diluent, such as acetonitrile, and if appropriate in the presence of an acid binder, such as sodium carbonate, Working up is carried out by customary methods.

The 1,2,3-benzothiadiazole derivatives of the formula (I) can be converted into acid addition salts and metal salt complexes.

The acids which have already been mentioned as preferred acids in connection with the description of the acid addition salts according to the invention can preferably be used to prepare acid addition salts of the compounds of the formula (I).

The acid addition salts of the compounds of the formula (I) can be obtained in a simple manner by customary salt formation methods, for example by dissolving a compound of the formula (I) in a suitable inert solvent and adding the acid, for example hydrochloric acid, and can be isolated in a known manner, for example by filtration, and if appropriate be purified by washing with an inert organic solvent.

Those salts of metals which have already been mentioned as preferred metal salts in connection with the description of the metal salt complexes according to the invention can preferably be used to prepare metal salt complexes of the compounds of the formula (I).

The metal salt complexes of the compounds of the formula (I) can be obtained in a simple manner by customary processes, thus, for example, by dissolving the metal salt in alcohol, for example ethanol, and adding the solution to compounds of the formula (I). The metal salt complexes can be isolated in a known manner, for example by filtration, and if appropriate be purificated by recrystallization.

The compounds according to the present invention exhibit a strong microbicidal activity and thus can be used for combating undesired microorganisms, such as phytopathogenic fungi and bacteria, in agriculture and horticulture. The compounds are suitable for the direct control of undesired microorganisms as well as for generating resistance in plants against attack be undesirable microorganisms.

Resistance-inducing substances in the present connection are to be understood as those substances which are capable of stimulating the defense system of plants such that the treated plants, when subsequently inoculated with undesirable microorganisms, display substantial resistance to these microorganisms. Undesirable microorganisms in the present case are to be understood as phytopathogenic fungi and bacteria. The substances according to the invention can thus be employed to generate resistance in plants against attack by the harmful organisms mentioned within a certain period of time after the treatment. The period of time within which resistance is brought about in general extends from 1 to 10 days, preferably 1 to 7 days, after treatment of the plants with the active compounds.

Generally, the compounds according to the invention can be used as fungicides for combating phytopathogenic fungi, such as Plasmodiophoromycetes, Oomycetes, Chytridiomycetes, Zygomycetes, Ascomycetes, Basidiomycetes and Deuteromycetes, and can also be used as bactericides for combating bacteria, such as Pseudomonoadaceae, Rhizobiaceae, Enterobacteriaceae, Corynebacteriaceae and Streptomycetaceae.

Some causative organisms of fungal and bacterial diseases included under the above-mentioned main headings, are mentioned below as non-limiting examples: Xanthomonas species, such as, for example, *Xanthomonas campestris* pv.*oryzae*; Pseudomonas species, such as, for example, *Pseudomonas syringae* pv.*lachrymans*; Erwinia species, such as, for example, *Erwinia amylovora*; Pythium species, such as, for example, *Pythium ultimum*; Phytophthora species, such as, for example, *Phytophthora infestans*; Pseudoperonospora species, such as, for example, *Pseudoperonospora cubensis*; Plasmopara species, such as, for example, *Plasmopara viticola*; Peronospora species, such as, for example, *Peronospora pisi* or *P. brassicae*; Erysiphe species, such as, for example, *Erysiphe graminis*; Sphaerotheca species, such as, for example, *Sphaerotheca fuliginea*; Podosphaera species, such as, for example, *Podosphaera leucotricha*; Venturia species, such as, for example, *Venturia inaequalis*; Pyrenophora species, such as, for example, *Pyrenophora teres* or *P. graminea*; (Conidial form: Drechslera, Synonym: Helminthosporium); Cochliobolus species, such as, for example, *Cochliobolus sativus*; (Conidial form: Drechslera, Synonym: Helminthosporium); Uromyces species, such as, for example, Uromyces appendiculatus; Puccinia species, such as, for example, *Puccinia recondita*; Tilletia species, such as, for example, Tilletia caries; Ustilago species, such as, for example, *Ustilago nuda* or *Ustilago avenae*; Pellicularia species, such as, for example, *Pellicularia sasakii*; Pyricularia species, such as, for example, *Pyricularia oryzae*; Fusarium species, such as, for example, *Fusarium culmorum*; Botrytis species, such as, for example, *Botrytis cinerea*; Septoria species, such as, for example, *Septoria nodorum*; Leptosphaeria species, such as, for example, *Leptosphaeria nodorum*; Cercospora species, such as, for example, *Cercospora canescens*; Alternaria species, such as, for example, *Alternaria brassicae*; Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

The active compounds can be converted into the customary formulations, such as solutions, emulsions, wettable powders, suspensions, powders, foams, pastes, granules, tablets, aerosols, natural and synthetic materials impregnated with active compound, very fine capsules in polymeric substances, coating compositions for use on seed, and formulations used with burning equipment, such as fumigating cartridges, fuirgating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, there are suitable in the main, aromatic hydrocarbons, such as xylene, toluene or alkyl napthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl-isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products.

Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 per cent by weight of active compound, preferably from 0.5 to 90 per cent by weight.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomising, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, from 1 to 0.0001% by weight, preferably from 0.5 and 0.001%.

For the treatment of seed, amounts of active compound of 0.001 to 50 g, especially 0.01 to 10 g, are generally employed per kilogram of seed.

For the treatment of soil, active compound concentrations, at the point of action, of 0.00001 to 0.1% by weight, especially of 0.0001 to 0.02%, are generally employed.

The preparation and use of the active compounds according to the invention can be seen from the following examples.

SYNTHESIS EXAMPLE 1

(Compound No. 2)

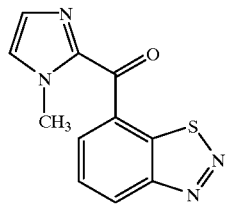

(Process b):

2-(3'-Amino-2'-benzylthio-benzoyl)-1-methylimidazole (7.5 g) was added to concentrated hydrochloric acid (24 ml) in water (10 ml) at 40° C. The mixture was stirred at 40° C. for 20 minutes and then cooled to −5° C. A solution of sodium nitrite (1.6 g) in water (10 ml) was added dropwise thereto. After the completion of the addition, the mixture was stirred at 0° C. for 2 hours and stirred further for 2 hours at room temperature. The reaction solution was extracted twice with dichloromethane. The extract was washed with water and dried over anhydrous sodium sulfate. The organic phase was concentrated under reduced pressure and the remaining residue was purified by silica gel column chromatography (eluting solvent:chloroform). 2-(1',2',3'-Benzothiadiazol-7'-yl)-carbonyl-1-methylimidazole (1.2 g) was obtained in this manner.

Melting point: 187–188.5° C.

Synthesis Example 2

(Compound No. 2)

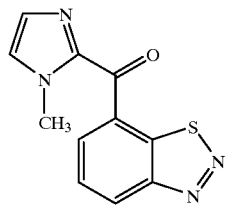

(Process a):

9.9 g of 7-Chlorocarbonyl-1,2,3-benzothiadiazole were added dropwise to a solution of 4.1 g of 1-methyl-imidazole and 4.4 g of pyridine in 300 ml of dichloromethane, while stirring and cooling with ice. After the completion of the reaction, the reaction mixture was subsequently washed with 3% aqueous hydrochloric acid solution, 3% aqueous sodium hydroxide solution and water. The organic layer was dried over anhydrous sodium sulfate. The organic layer was then concentrated under reduced pressure and purified by silica gel column chromatography (eluting solvent:chloroform). 2-(1',2',3'-Benzothiadiazol-7'-yl)-carbonyl-1-methylimidazole (1.2 g) was obtained in this manner.

Melting point: 187–188.5° C.

SYNTHESIS EXAMPLE 3

(Compound No. 17)

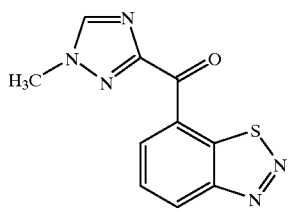

(Process d):

A mixture of 3-(1',2',3'-benzothiadiazol-7'-yl)-carbonyl-1,2,4-triazole (1.2 g), acetonitrile (50 ml), calcium carbonate (0,7 g) and methyl iodide (0.7 g) was heated under stirring for 3 hours. The reaction mixture was then evaporated to dryness under reduced pressure and the residue was purified by silica gel column chromatography (eluting solvent:chloroform). 3-(1',2',3'-Benzothiadiazol-7'-yl)-carbonyl-1-methyl-1,2,4-triazole (1.3 g) was obtained in this manner.

Melting point: 196–198° C.

SYNTHESIS EXAMPLE 4

(Compound No. 12)

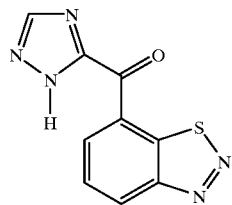

(Process c):

5-(1',2',3'-Benzothiadiazol-7'-yl)-carbonyl-1-methoxymethyl-1,2,4-triazole (2 g) was added to concentrated hydrochloric acid (100 ml), and the mixture was heated under stirring at 80–90° C. for 30 minutes. The reaction mixture was then evaporated to dryness under reduced pressure and the residue was recrystallized from ethanol. 5-(1',2',3'-Benzothiadiazol-7'-yl)-carbonyl-1,2,4-triazole (1.2 g) was obtained in this manner.

Melting point: >300° C.

The following Table 2 shows compounds of the formula (I), which were synthesized according to the processes mentioned above.

TABLE 2

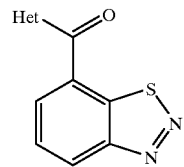
(I)

| Compound No. | Het | Melting point (° C.) |
|---|---|---|
| 1 | 2-methyl-1-vinyl-imidazol-yl | 196–199 |
| 2 | 1,2-dimethyl-imidazol-yl | 187–188.5 |
| 3 | 1-isopropyl-2-methyl-imidazol-yl | 152.5–155 |
| 4 | 1-cyanomethyl-2-methyl-imidazol-yl | 223.5–225.5 |
| 5 | 1-(2-cyanoethyl)-2-methyl-imidazol-yl | 235.5–237 |
| 6 | 1-methoxymethyl-2-methyl-imidazol-yl | 112–114.5 |
| 7 | 2-methyl-thiazol-yl | 174–175.5 |
| 8 | 2,5-dimethyl-thiazol-yl | 220.5–222 |
| 9 | 2,4,5-trimethyl-thiazol-yl | 184.5–186 |

TABLE 2-continued

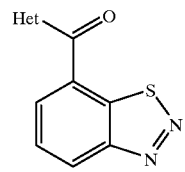
(I)

| Compound No. | Het | Melting point (° C.) |
|---|---|---|
| 10 | 1,5-dimethyl-1,2,4-triazol-yl | 154.5–158 |
| 11 | 1-isopropyl-5-methyl-1,2,4-triazol-yl | 90.5–100.5 |
| 12 | 3-methyl-1H-1,2,4-triazol-yl | >300 |
| 13 | 1-methoxymethyl-5-methyl-1,2,4-triazol-yl | 123–125 |
| 14 | 1-ethyl-5-methyl-1,2,4-triazol-yl | 131.5–133 |
| 15 | 5-methyl-1-propyl-1,2,4-triazol-yl | 125.5–127.5 |
| 16 | 1-isopropyl-3-methyl-1,2,4-triazol-yl | 205.5–207.5 |
| 17 | 1-cyanomethyl-3-methyl-1,2,4-triazol-yl | 187 |

TABLE 2-continued (I)

Het—C(=O)— [benzothiazole ring substituent]

| Compound No. | Het | Melting point (°C.) |
|---|---|---|
| 18 | 3-methyl-1-methyl-1,2,4-triazol-5-yl | 196–198 |
| 19 | 5-methyl-1-methyl-1,2,4-triazol-3-yl | 188–190 |

PREPARATION OF INTERMEDIATES

SYNTHESIS EXAMPLE 5

Starting material for the compound of Synthesis Example 1:

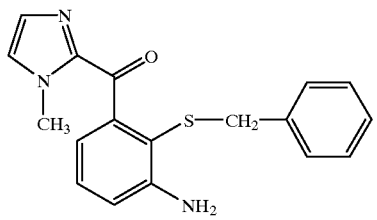

(IV-1)

2-(2'-Benzylthio-3'-nitrobenzoyl)-1-methylimidazole (8.6 g) was hydrogenated in ethanol in the presence of 5% palladium-carbon (6.0 g). After the completion of the reaction, the catalyst was separated by filtration and the solution was distilled under reduced pressure. 2-(3'-Amino-2'-benzylthiobenzolyl)-1-methylimidazole (8.0 g) was obtained in this manner.

Refractive index: $n_D^{20}=1.6513$.

SYNTHESIS EXAMPLE 6

Starting material for the compound of Synthesis Example 5:

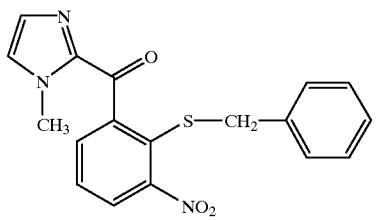

(VI-1)

Benzylmercaptan (4.3 g) and potassium carbonate (4.8 g) were added to a solution of 2-(2'-chloro-3'-nitro-benzoyl)-1-methyl-imidazole (9.2 g) in 150 ml of N,N-dimethylformamide. The reaction mixture was stirred at 80° C. for 5 hours. Then, the reaction mixture was poured onto ice water, and the resulting mixture was extracted twice with ethyl acetate. The combined organic phases were washed with water and then dried over anhydrous sodium sulfate. The organic phase was concentrated under reduced pressure and the remaining residue was purified by silica gel column chromatography (eluting solvent:hexane/ethyl acetate=95:5 v/v). 2-(2'-Benzylthio-3'-nitrobenzoyl)-1-methylimidazole (8.7 g) was obtained in this manner.

Refractive index: $n_D^{20}=1.6575$.

SYNTHESIS EXAMPLE 7

Starting material for the compound of Synthesis Example 6:

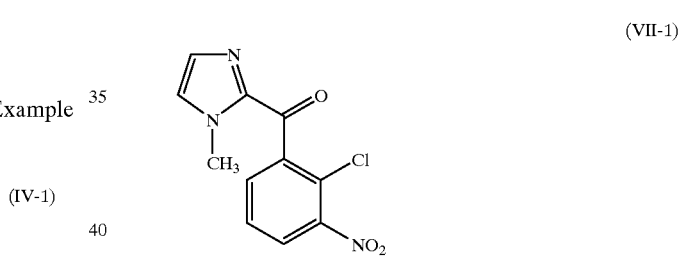

(VII-1)

2-Chloro-3-nitro-benzoyl chloride (10.9 g) was added dropwise to a solution of triethylamine (5.0 g) and I-methyl-imidazole (4.1 g) in 200 ml of dichloromethane, while stirring and cooling with ice. The reaction mixture was stirred at room temperature for 8 hours, and then it was washed consecutively with 3% aqueous hydrochloric acid, 3% aqueous sodium hydroxide solution and water. The organic layer was concentrated under reduced pressure and the remaining residue was purified by silica gel column chromatography (eluting solvent:chloroform/ethanol=99:1 v/v). 2-(2'-Chloro-3'-nitrobenzoyl)-1-methylimiazole (9.8 g) was obtained in this manner.

Melting point: 149–155.5° C.

BIOLOGICAL TEST EXAMPLES

Test Example A

Test of Foliar Spray Effect Against Rice Blast
Preparation of Formulations of the Compounds Tested
Active compound: 30–40 parts by weight
Carrier: Mixture of diatomaceous earth and kaolin (1:5), 55–65 parts by weight
Emulsifier: polyoxyethylene alkyl phenyl ether, 5 parts by weight Each of the wettable powders is prepared by pulverizing and mixing the above amounts of active compound, carrier and emulsifier. A portion of the wettable powder containing the prescribed amount of the active compound is diluted with water to be subjected to the test mentioned below.

Testing Procedure

Seedlings of paddy rice (cultivar:Kusabue) were cultured in plastic pots each having a diameter of 7 cm. The previously prepared solution of the prescribed concentration of active compound was sprayed at a rate of 50 ml per 3 pots over the foliage of the seedlings in the 1.5 leaf stage. 10 Days after the application, a suspension of artificially cultured *Pyricularia oryzae* spores was spray-inoculated on the seedlings, and the seedlings were maintained at 25° C. and 100% relative humidity for infection. 7 Days after the inoculation, the infection degree per pot was examined and rated according to the following criteria. Further, the control value (%) was calculated. Furthermore, the phytotoxicity was concurrently examined. The results are shown in Table 3 below. The data in Table 3 are average values of the results of 3 pots in one plot.

| Degree of Infection | Percentage of Lesion area (%) |
|---|---|
| 0 | 0 |
| 0.5 | less than 2 |
| 1 | 2–less than 5 |
| 2 | 5–less than 10 |
| 3 | 10–less than 20 |
| 4 | 20–less than 40 |
| 5 | not less than 40 | control value (%)=(1-(degree of infection in treated plot ./.degree of infection in non-treated plot))×100

Test Example B

Test of Water Surface Application Effect Against Rice Blast

Testing Procedure

Seedlings of paddy rice (cultivar:Kusabue) in the 1.5 leaf stage were transplanted into irrigated plastic pots (100 cm²), one seedling per pot. 7 Days after the transplanting (when the seedlings were in the 3–4 leaf stage), the solution of the prescribed concentration of the active compound, which had been prepared in the manner similar to that of Test Example A, was dropped at a rate of 10 ml per pot, with a pipette, to the water surface. 20 Days after the chemical treatment, a suspension of artificially cultured rice blast (blast fungus race C) spores was spray-inoculated twice on the seedlings, and the seedlings were maintained in the inoculation box at 25° C. and 100% relative humidity for 12 hours for infection. Thereafter, the seedlings were transferred to the greenhouse for management. 10 Days after the inoculation, the degree of infection per pot was evaluated, and the control value (%) was calculated in the manner similar to that of Test Example A. Furthermore, the phytotoxicity was concurrently examined. The results are shown in Table 3 below.

Test Example C

Test of Spray Against Tomato Blight

Preparation of Formulations of Active Compounds

Active compound: 30–40 parts by weight

Carrier: mixture of diatomaceous earth and kaolin (1:5), 55–65 parts by weight

Emulsifier: polyoxyethylene alkyl phenyl ether, 5 parts by weight

Wettable powders are prepared by pulverizing and mixing the above amounts of active compound, carrier and emulsifier. A portion of the wettable powder containing the prescribed amount of the active compound is diluted with water to be subjected to the test mentioned below.

Testing Procedure

About 5 seeds of tomato (cultivar:Kurihara) were sown in each vinyl plastic pot of a diameter of 7 cm, and raised in a greenhouse (at 15–25° C.). The solution obtained by diluting the prepared formulation of the testing compound to the prescribed concentration as mentioned above, was sprayed at a rate of 25 ml per 3 pots over small seedlings reaching the 4 leaf stage. 10 Days after the spraying, the zoosporangia formed on lesions, which had previously been infected and diseased with *Phytophthora infestans*, were washed down with a writing-brush into distilled water to prepare a suspension. The suspension was spray-inoculated on the treated plants and they were maintained in a greenhouse at 15–20° C. 7 Days after the inoculation, the degree of infection per pot was evaluated and the control value was calculated in the manner similar to that of Text Example A. The phytotoxicity was concurrently examined. The results are shown in Table 3. The data are average values of the results of 3 pots in one plot.

Test Example D

Test of Spray Against Barley Powdery Mildew

Testing Procedure

About 10 seeds of barley (cultivar:Haruna 2jyo) were sown in each vinyl plastic pot of a diameter of 7 cm, and raised in a greenhouse at 15–25° C. The solution obtained by diluting the formulation of the testing compound which had been prepared in the manner similar to that of Test Example C, was sprayed at a rate of 25 ml per 3 pots over small seedlings reaching the 2 leaf stage. 5 Days after the spraying, the conidiospores formed on lesions, which had previously been infected and diseased with *Erysiphe graminis*, were sprinkled over the treated barley leaves for inoculation. The plants were kept in a greenhouse at 15–20° C. 7 Days after the inoculation, the degree of infection per pot was evaluated and the control value was calculated in the manner similar to that of Test Example A. The phytotoxicity was concurrently examined. The results are shown in Table 3. The data are average values of the results of 3 pots in one plot.

TABLE 3

| Compound No. | Test Example A | Test Example B | Test Example C | Test Example D |
|---|---|---|---|---|
| 1 | ++++ | ++++ | ++ | |
| 2 | +++ | ++++ | ++++ | ++ |
| 3 | ++++ | ++++ | +++ | |
| 4 | +++ | +++ | ++++ | +++ |
| 5 | +++ | +++ | ++++ | +++ |
| 6 | ++++ | ++++ | ++ | |
| 7 | +++ | ++++ | ++++ | +++ |
| 8 | +++ | +++ | ++++ | ++ |
| 9 | ++ | +++ | ++++ | +++ |
| 10 | +++ | ++++ | ++++ | +++ |
| 12 | +++ | +++ | +++ | ++ |
| 13 | ++ | ++ | ++++ | ++ |
| 16 | +++ | | +++ | |

In the Table:
++++: control value, 95% or higher
+++: control value, 85% or higher
++: control value, 70% or higher
+: control value, 50% or higher
In all the tests, no phytotoxicity was observed.

It will be understood that the specification and examples are illustrative but not limitative of the present invention and that other embodiments within the spirit and scope of the invention will suggest themselves to those skilled in the art.

What is claimed is:

1. A phenyl derivative of the formula

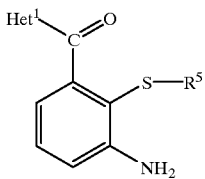

(IV)

in which

Het$^1$ represents

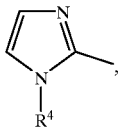

wherein

R$^4$ is C$_{1-4}$ alkyl, C$_{1-4}$-haloalkyl, phenyl-C$_{1-4}$ alkyl, cyano-C$_{1-4}$ alkyl, C$_{1-2}$-alkoxy-C$_{1-4}$, alkyl, C$_{1-2}$ alkylthio-C$_{1-4}$ alkyl, C$_{1-2}$-alkoxy-carbonyl-C$_{1-4}$ alkyl, C$_{2-4}$ alkenyl, phenyl, halogen substituted phenyl or C$_{1-4}$ alkyl substituted phenyl, and R$^5$ is hydrogen, C$_{1-4}$ alkyl, benzyl or acetyl.

2. A nitro-phenyl derivative of the formula

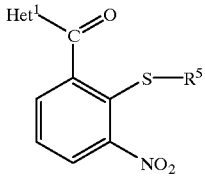

(VI)

in which

Het$^1$ represents

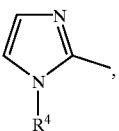

wherein

R$^4$ is C$_{1-4}$ alkyl, C$_{1-4}$-haloalkyl, phenyl-C$_{1-4}$ alkyl, cyano-C$_{1-4}$ alkyl, C$_{1-2}$-alkoxy-C$_{1-4}$ alkyl, C$_{1-2}$ alkylthio-C$_{1-4}$ alkyl, C$_{1-2}$-alkoxy-carbonyl-C$_{1-4}$ alkyl, C$_{2-4}$ alkenyl, phenyl, halogen substituted phenyl or C$_{1-4}$ alkyl substituted phenyl, and R$^5$ is hydrogen, C$_{1-4}$ alkyl, benzyl or acetyl.

3. A chloro-nitro-phenyl derivative of the formula

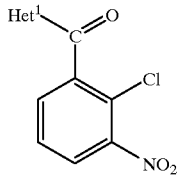

(VII)

in which

Het$^1$ represents

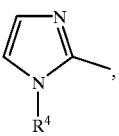

wherein

R$^4$ is C$_{1-4}$ alkyl, C$_{1-4}$-haloalkyl, phenyl-C$_{1-4}$ alkyl, cyano-C$_{1-4}$ alkyl, C$_{1-2}$-alkoxy-C$_{1-4}$ alkyl, C$_{1-2}$ alkylthio-C$_{1-4}$ alkyl, C$_{1-2}$-alkoxy-carbonyl-C$_{1-4}$ alkyl, C$_{2-4}$ alkenyl, phenyl, halogen substituted phenyl or C$_{1-4}$ alkyl substituted phenyl.

* * * * *